United States Patent
Van Horn et al.

(10) Patent No.: US 10,377,807 B2
(45) Date of Patent: Aug. 13, 2019

(54) HEAT-SENSING PROTEIN SWITCHES AND USES THEREOF

(71) Applicants: Wade Dale Van Horn, Mesa, AZ (US); Minjoo Kim, Mesa, AZ (US)

(72) Inventors: Wade Dale Van Horn, Mesa, AZ (US); Minjoo Kim, Mesa, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 307 days.

(21) Appl. No.: 15/191,902

(22) Filed: Jun. 24, 2016

(65) Prior Publication Data

US 2016/0376338 A1  Dec. 29, 2016

Related U.S. Application Data

(60) Provisional application No. 62/184,075, filed on Jun. 24, 2015.

(51) Int. Cl.
*C07K 14/705* (2006.01)
*G01N 33/68* (2006.01)

(52) U.S. Cl.
CPC ....... *C07K 14/705* (2013.01); *G01N 33/6872* (2013.01); *C07K 2319/00* (2013.01); *G01N 2500/04* (2013.01); *G01N 2500/10* (2013.01)

(58) Field of Classification Search
None
See application file for complete search history.

(56) References Cited

PUBLICATIONS

Choi et al., "Design of protein switches based on an ensemble model of allostery", Nature Communications, Apr. 2015, 6:6968. DOI: 10.1038/ncomms7968.*
Grandl et al., "Temperature-induced opening of TRPV1 ion channel is stabilized by the pore domain", Nature Neuroscience, Jun. 2010, 13(6): 708-715. DOI:10.103715/nn.2552.*
Cao et al., TRPV1 channels are intrinsically heat sensitive and negatively regulated by phosphoinositide lipids., Neuron, Feb. 2013, 77(4):667-79.
Caterina et al., The capsaicin receptor: a heat-activated ion channel in the pain pathway., Nature, Oct. 1997, 389(6653):816-24.
Liao et al., Structure of the TRPV1 ion channel determined by electron cryo-microscopy., Nature, Dec. 2013, 504:107-12.

* cited by examiner

*Primary Examiner* — Suzanne M Noakes
(74) *Attorney, Agent, or Firm* — Quarles & Brady LLP

(57) ABSTRACT

A region of the TRPV1 protein that functions as a temperature switch (FIG. 1) has been identified, and can be expressed, purified and applied in combination with other proteins. The function of the switch is maintained even when the region or domain is isolated from the entire protein. As the protein domain is a temperature switch, it can be used to control other proteins and signaling pathways in vitro and in vivo; and TRPV1 is a therapeutic target that is being pursued primarily for intervention in pain (neuropathic and inflammatory) and cancer.

9 Claims, 5 Drawing Sheets

(5 of 5 Drawing Sheet(s) Filed in Color)

HEAT-SENSING PROTEIN SWITCHES AND USES THEREOF

CROSS-REFERENCE TO RELATED APPLICATIONS

This application claims the benefit of U.S. Provisional Application Ser. No. 62/184,075, filed Jun. 24, 2015, which is incorporated by reference herein as if set forth in its entirety.

This invention was made with government support under R01 GM112077 awarded by the National Institutes of Health. The government has certain rights in the invention.

BACKGROUND

Transient receptor potential cation channel subfamily V member 1 (TRPV1) is a receptor for capsaicin and a non-selective cation channel structurally related to members of the transient receptor potential (TRP) family of ion channels. TRPV1 is modulated by various physical and chemical stimuli such as mild voltage, endogenous lipids, small proteins, pH, and capsaicin, and is also activated by increases in temperature in the noxious range, indicating it functions as a transducer of painful thermal stimuli in vivo. Due to its sensitivity to some noxious stimuli, TRPV1 is an excellent therapeutic target especially for pain. However, it was previously unknown how capsaicin interacts with TRPV1 or drives ion channel activation.

SUMMARY OF THE INVENTION

The embodiments described herein relate to regulation of protein domains, specifically the controlled regulation of membrane proteins by thermosensitive voltage-sensitive domains.

In a first aspect, provided herein is a method of regulating protein conformation, the method comprising associating a protein and a temperature sensitive protein domain to form a protein switch, where regulating a conformation of the protein switch comprises changing a temperature of the protein switch such that the protein switch conformation at a changed temperature varies from the protein switch conformation at an initial temperature. The temperature sensitive domain can comprise a Transient Receptor Potential Cation channel subfamily V member 1 (TRPV1) protein domain. The protein can comprise a membrane protein domain. Associating can comprise fusing the protein to the temperature sensitive domain to form the protein switch. The method can further comprise detecting the varied protein switch conformation at the changed temperature by HSQC NMR. The changed temperature of the protein switch can comprise the initial temperature increased by about 2° C. The changed temperature of the protein switch can comprise the initial temperature decreased by about 2° C. The changed temperature can comprise about 20° C. The changed temperature can comprise about 30° C. The changed temperature can comprise about 40° C. The changed temperature can comprise about 50° C.

In another aspect, provided herein is an in vitro or in situ method for identifying an agent that inhibits or suppresses transduction of painful thermal stimuli, the method comprising (a) contacting a test compound with a cell comprising a TRPV1 sensing domain, and (b) identifying whether said compound inhibits a signaling activity of an activated TRPV1 in the cell in response to exposure to a temperature above physiological temperature, thereby identifying an agent that inhibits or suppresses transduction of painful thermal stimuli.

In a further aspect, provided herein is a kit for protein conformation regulation comprising: an isolated temperature sensing protein domain, the temperature sensitive domain configured to regulate a protein conformation during a temperature change from an initial temperature to a changed temperature. The temperature sensitive domain can comprise a TRPV1 protein domain. The changed temperature can comprise about 20° C. The changed temperature can comprise about 50° C.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein.

The patent or application file contains at least one drawing executed in color. Copies of this patent or patent application publication with color drawings(s) will be provided by the Office upon request and payment of the necessary fee.

Figure 1:
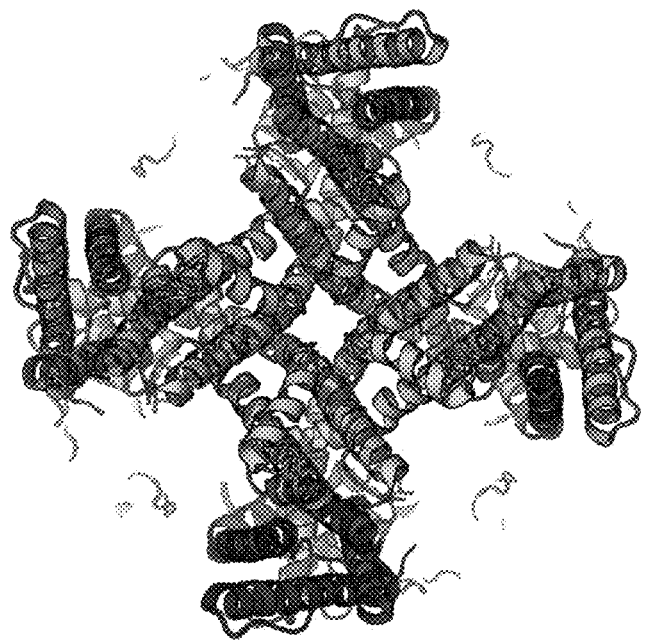
FIG. 1 presents transmembrane helices S1-S4, comprising the sensing domain of TRPV1.
Figure 1:
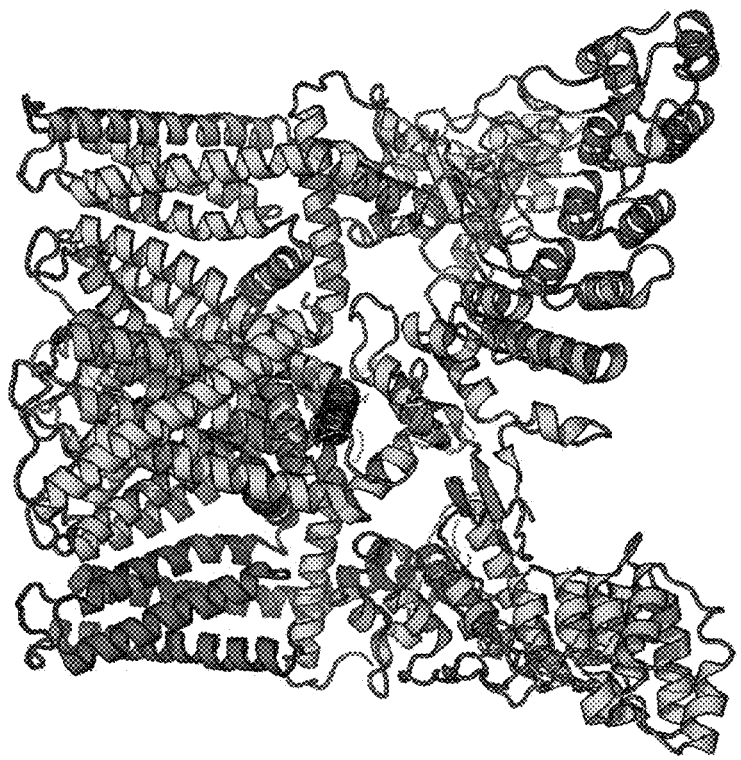
Figure 2:
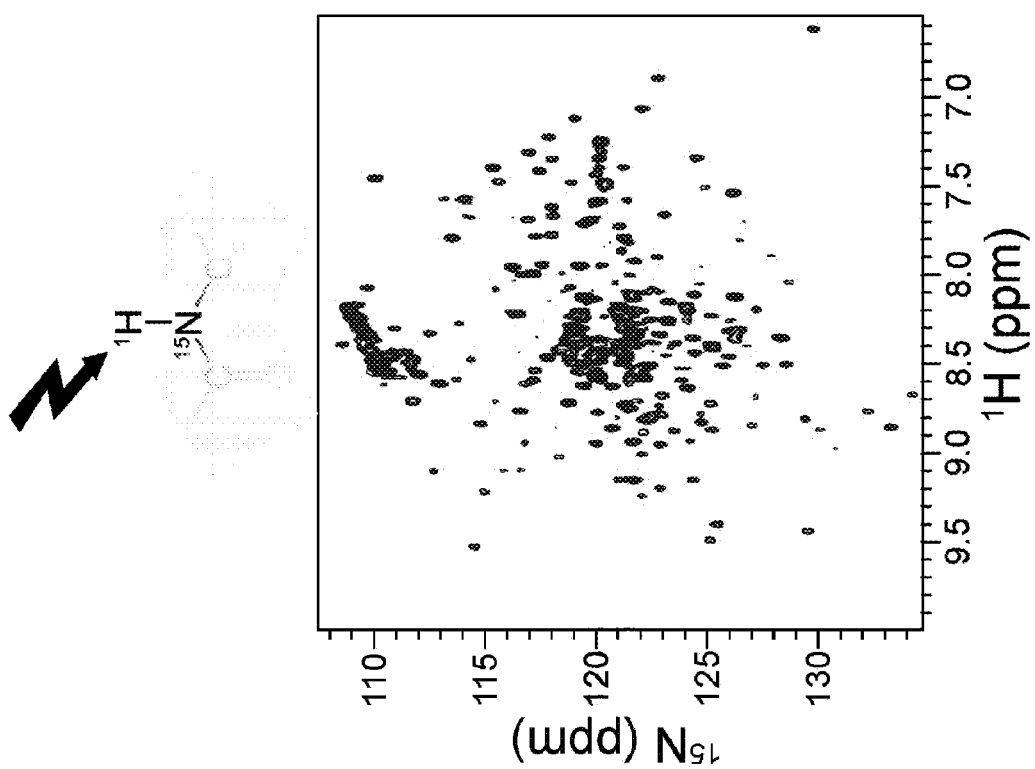
FIG. 2 illustrates a general Heteronuclear Single Quantum Coherence (HSQC) experiment using isotopically labeled proteins and NMR. The resulting two-dimensional (2D) spectrum has one axis for proton ($^1$H) and the other axis for $^{15}$N isotope (heteronucleus).

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

Embodiments described herein relate to gene products, specifically gene products that function as thermosensors. The embodiments described herein are based at least in part on the inventors' discovery of the temperature sensing domain of TRPV1, which is the single domain responsible for thermosensitivity and ion channel regulation. This invention is the first isolation of a protein-based temperature switch useful for temperature ranges above physiological temperature. The ability to control expression and function of the thermosensor of TRPV1 is the key to developing protein-based temperature switches useful in various forms of thermoregulation. The isolated temperature sensing domain has practical applicability as a molecular switch and as an element in drug screening against specific conformations of TRPV1. Accordingly, embodiments described in this disclosure provide temperature sensitive molecular switches and methods for identifying, selecting, and using such molecular switches to screen and identify agents that affect molecular folding, bonding, or stability as a function of temperature. With respect to drug screening, the temperature sensitive molecular switches provided herein offer a simplified, conformational state-specific screening platform.

As used herein, the term "molecular switch" refers to a molecule which generates a change in state in response to a signal (e.g., a temperature or change in temperature). In one aspect, a molecular switch is capable of a switch or change in conformation or activity from at least one state to at least one other state in response to the signal. In a particular embodiment of the present invention, the protein switch is a temperature sensitive polypeptide comprising a thermosensing domain. The ability to create novel protein switches or to modify existing protein switches by coupling previously uncoupled protein functions has tremendous practical potential for developing novel molecular sensors, medical diagnostics and as a tool for elucidating molecular and cellular functions. A molecular switch also can comprise a plurality of fusion molecules responsive to a signal (e.g., a temperature or change in temperature) and which mediate a function by changing the state of at least a portion of the molecule (preferably, in response to a change in state of another portion of the molecule).

FIG. 1 illustrates crystallographic views of transmembrane helices S1-S4 of TRPV1, and illustrates the amino acids that comprise the transmembrane TRPV1 protein domain that provide the thermosensitivity of the protein domain.

Figure 3:
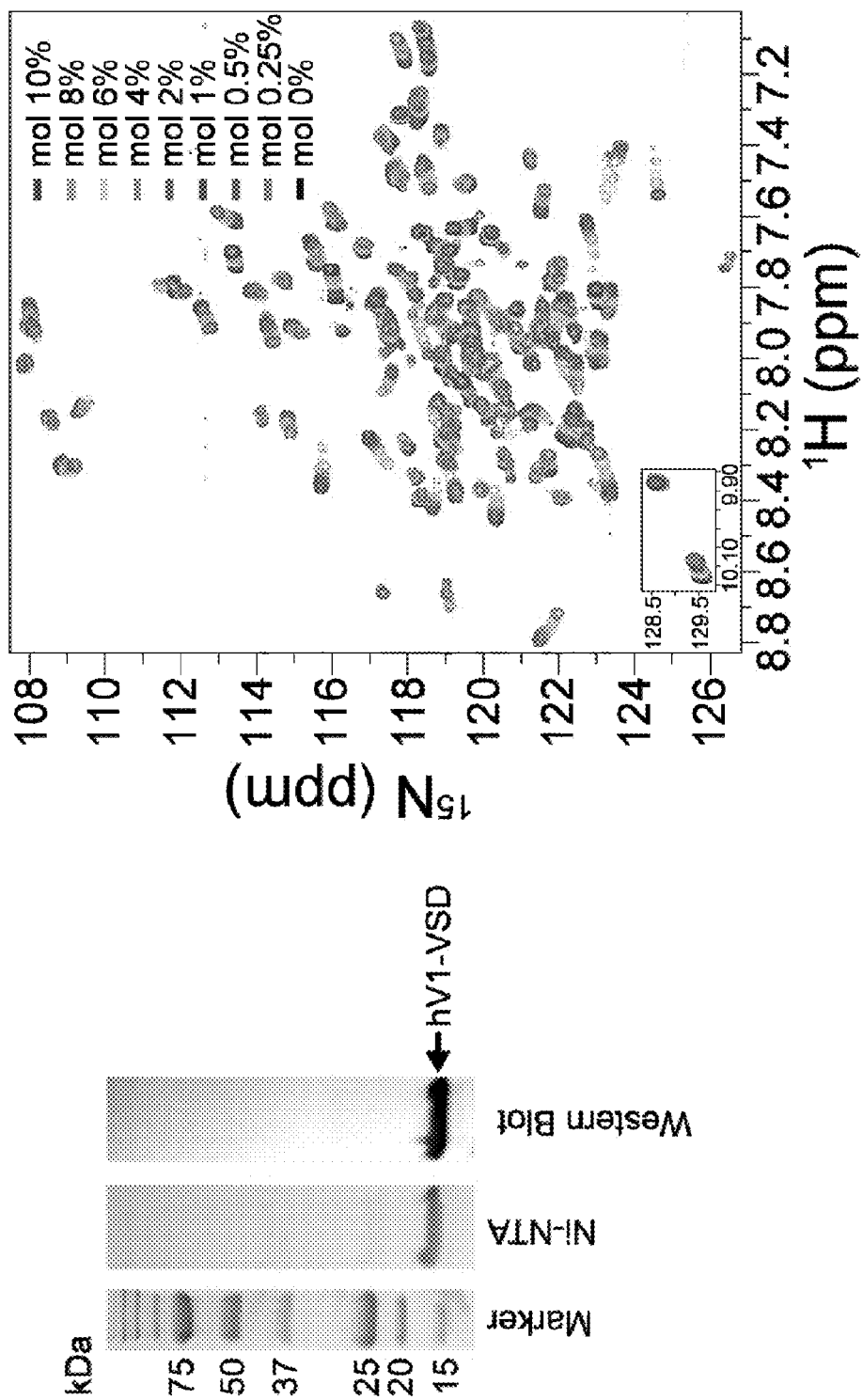
FIG. 3 presents capsaicin titration and HSQC-NMR data demonstrating that TRPV1 is properly folded.
Figure 4:
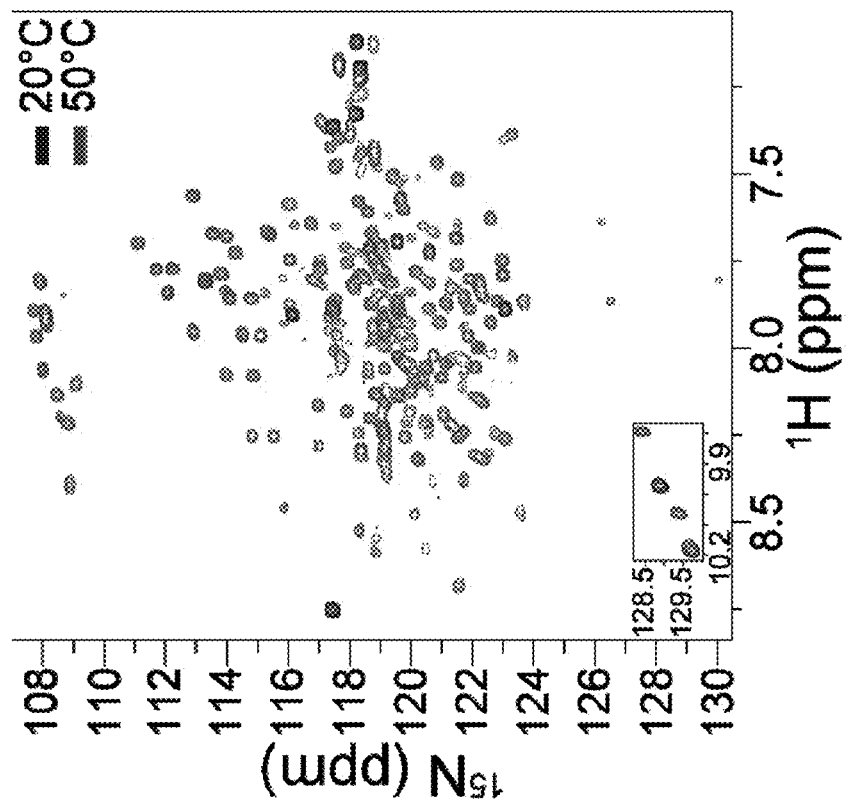
FIG. 4 presents HSQC-NMR data as a function of temperature.

The TRPV1 sensing domain changes conformational structure as a function of temperature, specifically around between room temperature and slightly above physiological temperature. Similarly, the protein conformation modulation of TRPV1-SD over a change in temperature (20° C. and 50° C.) can be observed in the HSQC NMR spectra of FIG. 3. In some cases, the TRPV1 sensing domain changes conformational structure in response to a temperature increase between 20° C. and 50° C. (e.g., 20° C., 25° C., 30° C., 35° C., 40° C., 45° C., 50° C.).

Fusion of the thermosensing domain to other proteins provides a mechanism for regulate biomolecules as a function of temperature. As described in Example 1 below, we have engineered a gene fragment of a voltage-sensitive protein domain into a pET16b expression vector and transformed *E. coli* bacteria with this vector and then used the bacteria to express the voltage sensing domain. While the protein is expressed in a number of conditions, we have optimized the expression of the human TRPV1 sensing domain in BL21 DE3 competent cells at 18° C. The human TRPV1 sensing domain (hTRPV1-SD) underwent several purification steps, including Ni-NTA affinity chromatography and size exclusion chromatography, using a detergent. We currently obtain about 1.0-1.2 mg of pure hTRPV1-SD per liter of bacterial culture.

During this process we can incorporate the VSD into many membrane mimics and evaluate the functional aspects of this domain. Under multiple detergent conditions we see significant conformational change as a function of temperature as measured by HSQC NMR indicating that this is an intrinsic feature of this isolated TRPV1 domain. It is noteworthy that we identify structural perturbation in the regime where electrophsyiology has shown for the transition of the channel happens physiologically. In addition, biophysical techniques such as far UV CD isolate structural transitions that occur within about +/−2° C. of the physiological conformation change for the entire TRPV1 protein.

The TRPV1 sensing domain is useful in methods for screening candidate molecules using specific conformations of the temperature switch. Currently, there are polymorphic crystals that are available as molecular temperature switches but they are not compatible with biology nor could they be harnessed with the same precision to regulate molecular dynamics as a function of temperature. This invention is the first isolation of a protein-based temperature switch. With respect to drug screening, the heat-sensitive protein switches provided herein offer a simplified platform that is conformational state specific which should allow for enhanced compounds.

For drug screening, it is clear that isomerization of compounds can effect efficacy and off target effects. Having the ability to fine tune the conformational state of the target should increase the efficacy of screening and development.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a," "an," and "the" include plural reference unless the context clearly dictates otherwise. As well, the terms "a" (or "an"), "one or more" and "at least one" can be used interchangeably herein. It is also to be noted that the terms "comprising," "including," and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The present invention will be more fully understood upon consideration of the following non-limiting Examples.

EXAMPLES

Example 1: TRP Channel Thermosensing

We constructed a sensing domain of the human transient receptor potential cation channel subfamily V member 1 (TRPV1) gene product in order to probe its role as a thermosensor. The sensing domain (SD) of TRPV1 gene was engineered into a pET16b expression vector and was transformed into *E. coli* bacteria for the better expression. We optimized the expression of the human TRPV1 sensing domain, which is in BL21 DE3 competent cells at 18° C.

Cells were induced with 0.1 mM IPTG when the OD600 reaches about 0.5, and the cells were induced for 48 hours. Upon harvesting by centrifugation, the cells were lysed by sonication. In order to extract the membrane protein, we used 0.3% Empigen detergent in about 10 mL lysis buffer per 1 gram of cell pellet, then we separate the insoluble cell debris by centrifugation at 18,000 RPM for 20 minutes at 4° C. The human TRPV1 sensing domain (hTRPV1-SD) underwent several purification steps, including Ni-NTA affinity chromatography and size exclusion chromatography, using a detergent.

As a result of purification process, we obtained 1.0-1.2 mg of pure hTRPV1-SD per liter of liquid bacterial culture. We determined the best suitable membrane mimic for the hTRPV1-SD by observing HSQC NMR spectra. Multiple detergents exhibited conformational changes of TRPV1-SD as a function of temperature, but LPPG showed the most resolved NMR spectra with expected conformational changes at different temperatures. Conformational changes as a function of temperature were also observed by far-UV circular dichroism.

We also performed paramagnetic relaxation enhancement measurements in order to investigate the mechanism of thermosensing. These data show that the S4 helix moves, and this movement is coupled to the channel domain resulting in temperature-based activation. We used nitroxide spin label as the paramagnetic probe, and we can extract distance information between paramagnetic center and nuclei of interest. The use of this heterologously expressed protein could have significant utility in generating new methods to regulate proteins and signaling cascades by making chimeras between other proteins that are not currently thermosensitive. Also because TRPV1 has been identified as a protein involved in pain, inflammation, diabetes, and other pathophysiologies, having the ability to isolate the TRPV1 SD in a known conformation is useful for developing state specific therapeutics which would lead to more specific and potent drug discovery for the treatment and/or the prevention of conditions related to high levels of expression and/or activity of TRPV1. Similarly, the TRPV1 SD framework is useful for generating structural configurations useful for refining lead compounds.

Figure 5:
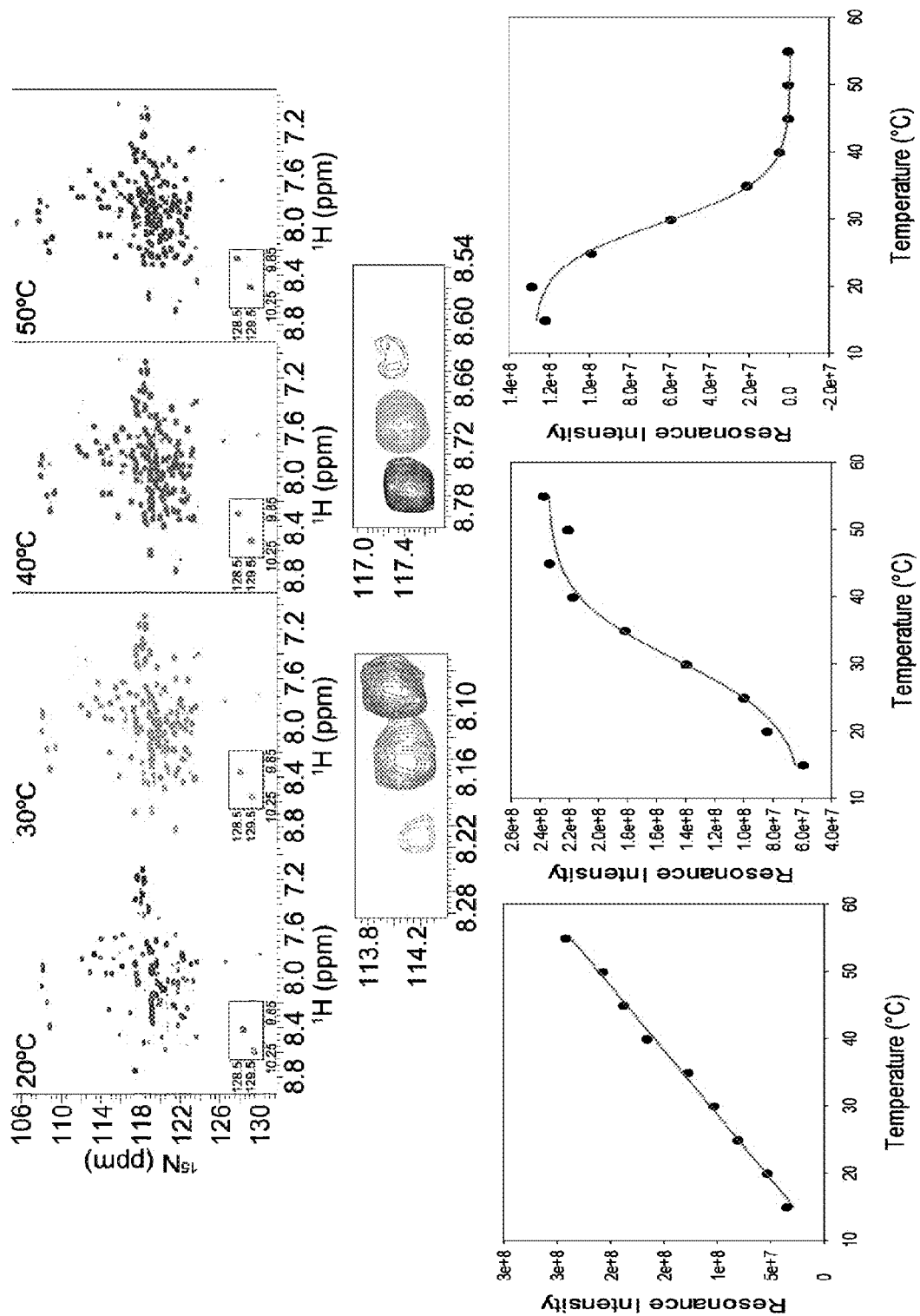
FIG. 5 presents HSQC-NMR data and resonance intensity data demonstrating identification of the "thermosensor" of TRPV1 without the use of mutations.

The data shown in FIG. 5 demonstrate discovery of the "thermosensor" of TRPV1 without the use of mutations that complicate the thermodynamic landscape.

In summary, this example demonstrates recombinant expression and purification of human TRPV1 VSD. Temperature studies indicated that the TRPV1 VSD undergoes temperature dependent conformational change. Consistent with a localized temperature sensor. VSD thermodynamics were sufficient to drive TRPV1 thermosensitivity. PRE studies lead us to conclude that the mechanism of TRPV1 thermosensing is analogous to established voltage-sensing mechanisms.

We claim:

1. A method of regulating a protein conformation comprising: producing a recombinant protein comprising a Transient Receptor Potential Cation channel subfamily V member 1 (TRPV1) protein temperature sensor domain fused to a heterologous protein, and regulating a conformation of the recombinant protein, wherein regulating comprises increasing or decreasing an initial first temperature of the recombinant protein such that the recombinant protein conformation at a changed second temperature varies from the recombinant protein conformation at the initial first temperature.

2. The method of claim 1, wherein the recombinant protein comprises a membrane protein domain.

3. The method of claim 1, further comprising detecting the varied protein conformation at the changed second temperature by HSQC NMR or circular dichroism.

4. The method of claim 1, wherein the changed second temperature of the recombinant protein comprises the initial first temperature increased by about 2° C.

5. The method of claim 1, wherein the changed second temperature of the recombinant protein comprises the initial first temperature decreased by about 2° C.

6. The method of claim 1, wherein the changed second temperature is about 20° C.

7. The method of claim 1, wherein the changed second temperature is about 30° C.

8. The method of claim 1, wherein the second temperature is about 40° C.

9. The method of claim 1, wherein the changed second temperature is about 50° C.

* * * * *

UNITED STATES PATENT AND TRADEMARK OFFICE
CERTIFICATE OF CORRECTION

PATENT NO. : 10,377,807 B2
APPLICATION NO. : 15/191902
DATED : August 13, 2019
INVENTOR(S) : Wade Dale Van Horn et al.

Page 1 of 1

It is certified that error appears in the above-identified patent and that said Letters Patent is hereby corrected as shown below:

In the Claims

Column 6, Claim 8, Line 39, "the second" should be --the changed second--.

Signed and Sealed this
Tenth Day of March, 2020

Andrei Iancu
*Director of the United States Patent and Trademark Office*